United States Patent
Chodkowski et al.

(10) Patent No.: US 11,724,055 B2
(45) Date of Patent: Aug. 15, 2023

(54) MULTI-LAYERS CUSHION ASSEMBLY FOR A PATIENT INTERFACE

(71) Applicant: KONINKLIJKE PHILIPS N.V., Eindhoven (NL)

(72) Inventors: Lauren Patricia Chodkowski, Pittsburgh, PA (US); Anna Dzuricky, Erie, PA (US); James Maier, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 731 days.

(21) Appl. No.: 16/822,408

(22) Filed: Mar. 18, 2020

(65) Prior Publication Data
US 2020/0306478 A1    Oct. 1, 2020

Related U.S. Application Data

(60) Provisional application No. 62/824,486, filed on Mar. 27, 2019.

(51) Int. Cl.
*A61M 16/06*    (2006.01)

(52) U.S. Cl.
CPC .... *A61M 16/0622* (2014.02); *A61M 16/0683* (2013.01); *A61M 16/0666* (2013.01); *A61M 2210/0618* (2013.01)

(58) Field of Classification Search
CPC .......... A61M 16/0622; A61M 16/0683; A61M 16/0666; A61M 2210/0618; A61M 16/06; A61M 16/0605; A61M 16/0611; A61M 16/0616
See application file for complete search history.

(56) References Cited

U.S. PATENT DOCUMENTS

| | | | |
|---|---|---|---|
| 9,308,343 B2 | 4/2016 | Groll et al. | |
| 2009/0211581 A1 | 8/2009 | Bansal | |
| 2010/0101584 A1 | 4/2010 | Bledstein et al. | |
| 2014/0182601 A1 | 7/2014 | Duffy | |
| 2017/0035978 A1* | 2/2017 | Holley | A61M 16/0605 |
| 2017/0049983 A1* | 2/2017 | Ellis | B32B 3/266 |

FOREIGN PATENT DOCUMENTS

| | | | |
|---|---|---|---|
| CN | 106723523 A | 5/2017 | |
| WO | WO-2013001083 A1 * | 1/2013 | A61F 5/01 |

* cited by examiner

*Primary Examiner* — Kendra D Carter
*Assistant Examiner* — Maap Ahmed Ellabib
(74) *Attorney, Agent, or Firm* — Michael W. Haas (57) ABSTRACT

A patient interface for use in delivering a flow of breathing gas to an airway of a patient. The patient interface includes a front portion and a rear portion coupled to the front portion. The front portion and the rear portion together define a cavity therebetween which is structured to receive the flow of breathing gas. The rear portion includes a support layer disposed directly adjacent the cavity, the support layer having a region having a plurality of first thru-holes structured to receive the flow of breathing gas from the cavity. The rear portion further includes a patient engaging layer structured to engage the patient at or about the airway of the patient, the patient engaging layer including at least a second thru-hole structured to receive the flow of breathing gas from the plurality of first thru-holes.

13 Claims, 7 Drawing Sheets

FIG.12

MULTI-LAYERS CUSHION ASSEMBLY FOR A PATIENT INTERFACE

CROSS-REFERENCE TO RELATED APPLICATIONS

This patent application claims the priority benefit under 35 U.S.C. § 119(e) of U.S. Provisional Application No. 62/824,486, filed on Mar. 27, 2019, the contents of which are herein incorporated by reference.

BACKGROUND OF THE INVENTION

1. Field of the Invention

The present invention relates to cushions for patient interface assemblies, such as, for example, patient interface assemblies used in airway pressure support systems.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion member on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

One known type of cushion for patient interface devices is a fabric cushion. Fabric cushions are often manufactured via laser cutting, a method that is efficient, but tends to produce fairly scratchy, burnt edges that can be uncomfortable to patients. Additionally, large openings such as one for a nostril or cradle opening for both nostrils, are also relatively difficult to align while sewing, and can thus be easily warped or deformed. Large openings in the fabric for providing patient therapy also tend to reduce the overall structure of the mask, which is something fabric masks in general already lack. Moreover, maintaining a strong seal is always important when delivering pressure support therapy.

SUMMARY OF THE INVENTION

Accordingly, it is an object of the present invention to provide a patient interface for use in delivering a flow of breathing gas to an airway of a patient. The patient interface comprises: a front portion; and a rear portion coupled to the front portion, the front portion and the rear portion together defining a cavity therebetween which is structured to receive the flow of breathing gas. The rear portion includes: a support layer disposed directly adjacent the cavity, the support layer comprising a region having a plurality of first thru-holes structured to receive the flow of breathing gas from the cavity, and a patient engaging layer structured to engage the patient at or about the airway of the patient. The patient engaging layer comprises at least a second thru-hole structured to receive the flow of breathing gas from the plurality of first thru-holes.

The second thru-hole may overlie only a portion of the region. The support layer may have an outer perimeter and the patient engaging layer may have an outer perimeter substantially overlaying the entire outer perimeter of the support layer and being coupled thereto. The patient engaging layer may be coupled to the support layer adjacent the second thru-hole. The patient engaging layer may be made of an elastic fabric material. The support layer may be made of a fabric material. The plurality of first thru-holes may comprise a dense array of thru-holes. The second thru-hole may comprise a dense array of thru-holes. The second thru-hole may comprise a first dense array of thru-holes structured to generally align with a first nare of a patient and a second dense array of thru-holes structured to generally align with a second nare of the patient. The second thru-hole may comprise a first thru-hole structured to generally align with a first nare of a patient and a second thru-hole structured to generally align with a second nare of the patient. The second thru-hole may be structured to generally align with both of the nares of a patient. Each of the plurality of first thru-holes may have a shape selected from the group consisting of circular-shaped, triangular-shaped, honeycomb-shaped, and rectangular-shaped. The support layer may comprise a mesh member coupled to the patient engaging layer adjacent the second thru-hole. The second thru-hole may comprise a first thru-hole structured to generally align with a first nare of a patient and a second thru-hole structured to generally align with a second nare of the patient and the support layer may comprise a first mesh member coupled to the patient engaging layer adjacent the first thru-hole and a second mesh member coupled to the patient engaging layer adjacent the second thru-hole.

It is another object of the present invention to provide an airway pressure support system for use in delivering a flow of a breathing gas to the airway of a patient. The airway pressure support system comprises: a gas flow generator structured to generate the flow of breathing gas; a hose having a first end coupled to the gas flow generator and an opposite second end; and a patient interface such as previously described coupled to the second end of the hose.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

As required, detailed embodiments of the present invention are disclosed herein; however, it is to be understood that the disclosed example embodiments described herein are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are coupled directly in contact with each other. As used herein, "fixedly coupled" or "fixed" means that two components are coupled so as to move as one while maintaining a constant orientation relative to each other.

As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
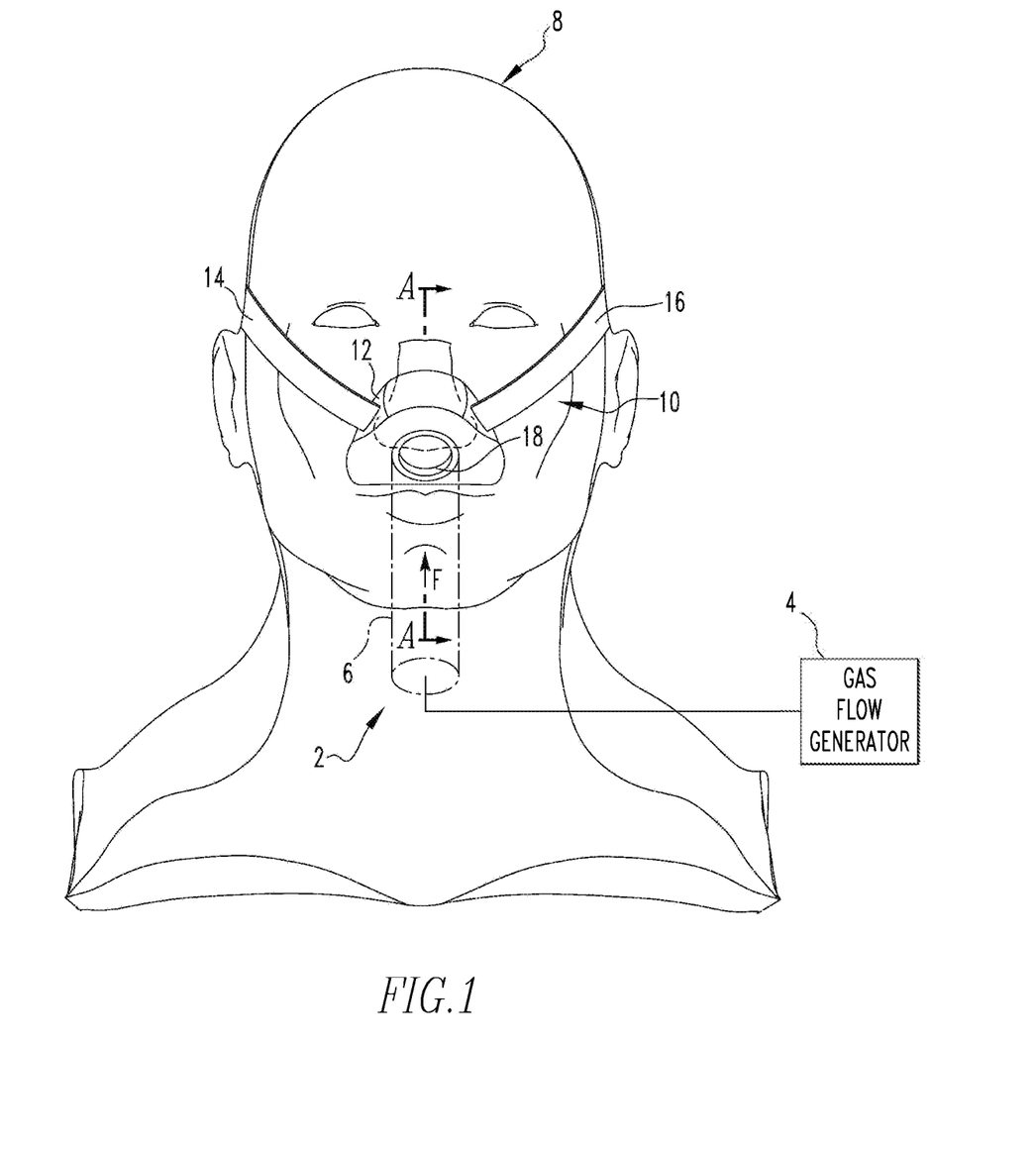
FIG. 1 is a simplified front view of an airway pressure support system having a patient interface in accordance with one non-limiting embodiment of the disclosed concept.

FIG. 1 is a simplified front view of an airway pressure support system 2 in accordance with one non-limiting embodiment of the disclosed concept shown disposed on the face of a patient 8. Airway pressure support system 2 includes a gas flow generator 4 (shown in simplified form) and a hose 6 (also shown in simplified form) having a first end (not numbered) coupled to gas flow generator 4 and an opposite second end (not numbered). Gas flow generator 4 is structured to generate a flow F of breathing gas to be delivered to an airway of patient 8 via hose 6 and a patient interface assembly 10. Accordingly, airway pressure support system 2 further includes patient interface assembly 10 for communicating the flow of breathing gas from hose 6 and gas flow generator 4 to the airway of patient 8.

Patient interface assembly 10 includes patient interface 12 which, in the example embodiment shown in FIG. 1, is secured to the face of patient 8 via a number of headgear straps 14, 16 which are also provided as parts of patient interface assembly 10. Although two headgear straps 14, 16 are shown in FIG. 1, it is to be appreciated that one or more of the quantity, placement, arrangement, etc. of headgear straps utilized with patient interface 12 may be varied without varying from the scope of the present invention. A connector member 18 (made of any suitable material, e.g., without limitation, a thermoplastic material) may be included as part of patient interface assembly 10 or hose 6 for use in coupling hose 6 and patient interface 12 such that flow F of breathing gas produced by gas flow generator 4 and conveyed by hose 6 may further be conveyed through patient interface 12 to the airway of patient 8.

Figure 1A:
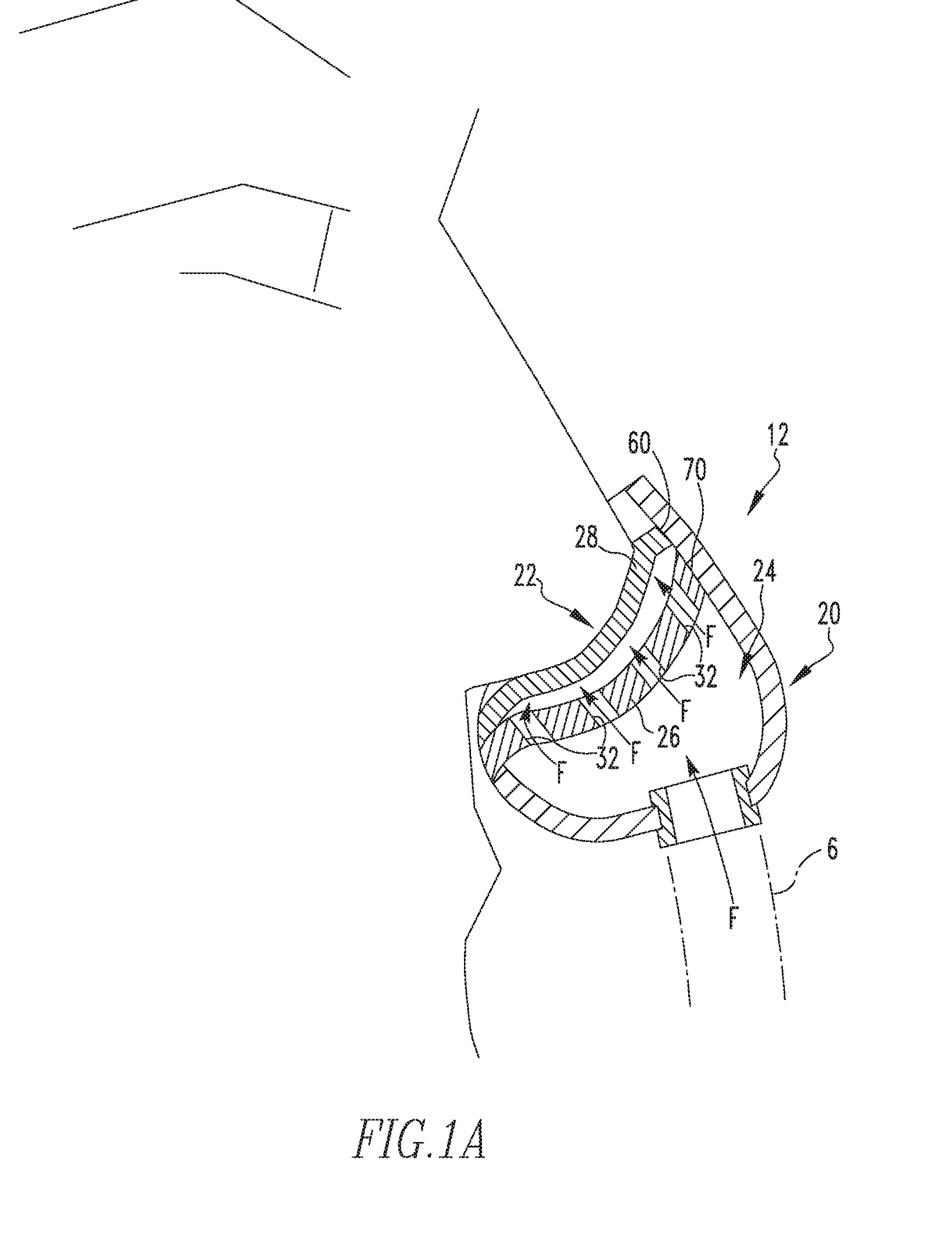
FIG. 1A is a simplified sectional view of the patient interface of FIG. 1 taken along line A-A of FIG. 1.
Figure 2:
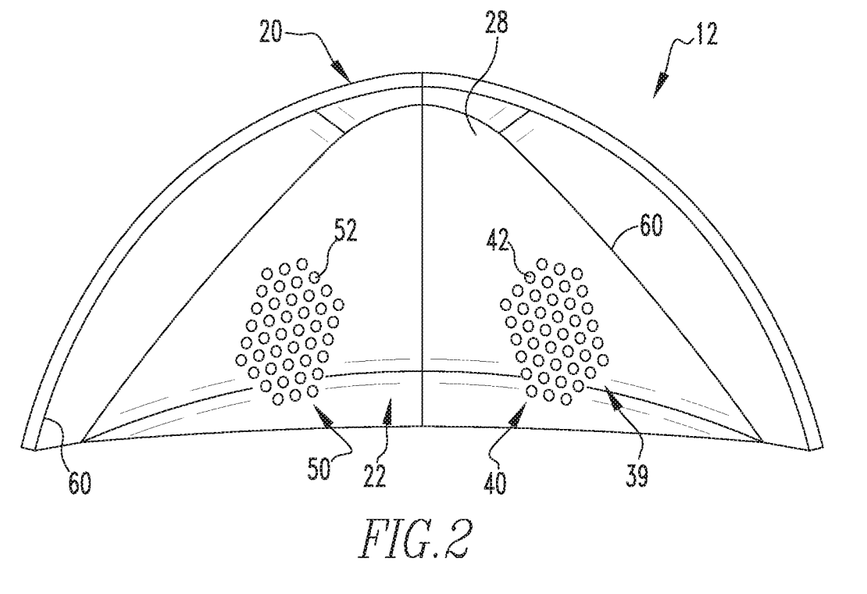
FIG. 2 is a simplified rear view of the patient interface of FIG. 1.
Figure 3:
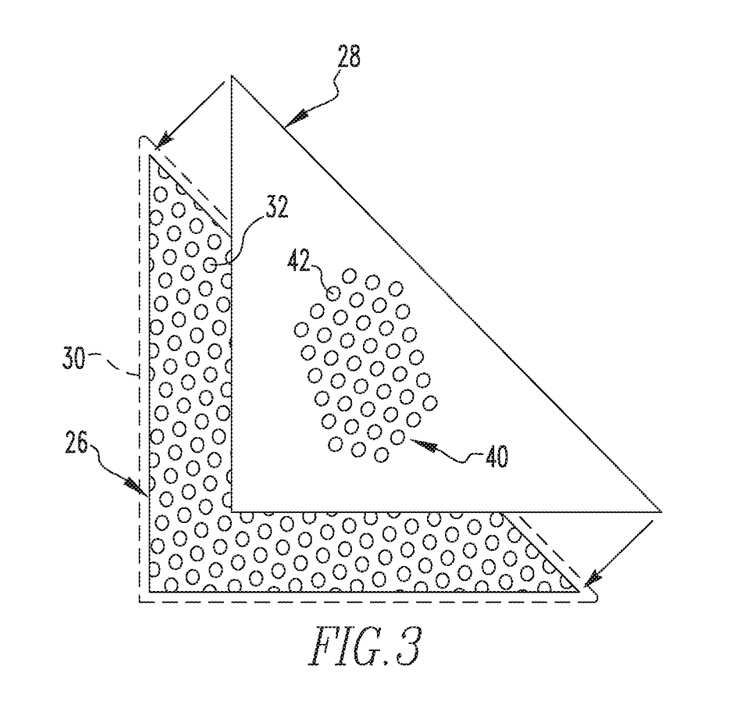
FIG. 3 is a simplified exploded view of a portion of a rear portion of the patient interface of FIG. 1 showing a patient engaging layer and support layer thereof.

Referring now to the views of FIGS. 1A, 2 and 3, patient interface 12 includes a front portion 20, that generally faces away from patient 8, and a rear portion 22, that generally faces patient 8. As shown in FIG. 1A, front portion 20 and rear portion 22 are coupled together such that a cavity 24, which is structured to receive the flow F of breathing gas from hose 6 produced by gas flow generator 4, is defined there between. Rear portion 22 includes a support layer 26 disposed directly adjacent cavity 24 and a patient engaging layer 28 disposed adjacent support layer 26, opposite cavity 24, so as to be positioned to directly engage patient 8 when patient interface 12 is disposed on the face of patient 8. In example embodiments of the present invention support layer 26 has been made of a fabric material (e.g., an impregnated or non-impregnated rip-soft nylon) and patient engaging layer 28 has been made of an elastic fabric material (e.g., a silicone backed elastic fabric material), however, it is to be appreciated that other suitable materials may be employed without varying from the scope of the present invention.

Referring now to the exploded view of FIG. 3, support layer 26 has a region 30 (enclosed by dashed line) having a plurality of thru-holes 32 (only one thru-hole 32 of the plurality is numbered) defined therein. In the example embodiment of FIG. 3, the plurality of thru-holes comprises a dense array of thru-holes, each having a diameter of about 1 mm or less (i.e., an area of about 3.14 mm$^2$ or less). The plurality of thru-holes 32 may be provided in support layer 26 via any suitable mechanism (e.g., laser cut, punched, etc.). As an alternative to particularly defined/formed thru-holes, support layer may be formed from a porous material through which flow F of breathing gas may pass. Materials having an open area of at least 20% have been found to be suitable.

Continuing to refer to FIG. 3 as well as FIG. 2, patient engaging layer 28 includes at least one thru-hole 39 which, in the example embodiment of FIG. 2, is a first dense array 40 of thru-holes 42 (only one thru-hole 42 of first dense array 40 is numbered) and a second dense array 50 of thru-holes 52 (only one thru-hole 52 of second dense array 50 is numbered). First and second dense arrays 40, 50 of thru-holes 42, 52 may be provided in patient engaging layer 28 via any suitable mechanism (e.g., laser cut, punched, etc.). In one example embodiment, each thru-hole 42, 52 of first and second dense arrays 40, 50 has a diameter of about 1 mm or less (i.e., an area of about 3.14 mm$^2$ or less). First dense array 40 of thru-holes 42 and second dense array 50 of thru-holes 52 are spaced from one another and are each positioned to generally align with a corresponding nare of patient 8 when patient interface 12 is positioned on the face of patient 8, such as shown in FIG. 1. It is to be appreciated that each of dense arrays 40 and 50 overlie only a portion of region 30 of support layer 26 disposed therebelow.

In the example embodiment illustrated in FIG. 1A, patient engaging layer 28 has an outer perimeter 60, and support layer 26 has an outer perimeter 70 coupled to outer perimeter 60 of patient engaging layer 28, generally away from first and second dense arrays 40 and 50. As a result of such arrangement, when patient interface 12 is donned by patient 8, flow F of breathing gas passes into cavity 24 from hose 6, through thru-holes 32 of support layer 26 and then exits patient interface through thru-holes 42 and 52 of each of dense arrays 40 and 50. As the thru-holes 32 of support layer 26 generally underlie the entirety of patient engaging layer 28, patient engaging layer 28 is generally inflated toward patient 8 away from support layer 26 and cavity 24, thus providing a cushiony seal about the nares of patient 8 and thereby minimizing leaks. Additionally, because thru-holes 42 and 52 of first and second dense arrays 40 and 50 are relatively small, e.g., each preferably having an opening area of less than 3.14 mm$^2$ (i.e., less than 1 mm diameter), the nose of patient 8 generally engages the surface of patient engaging layer 28 and raw edges of thru-holes 42 and 52 will not be felt to a large extent. Hence, the arrangement of FIGS. 1-3 provides for a soft, comfortable patient interface 12.

Figure 4:
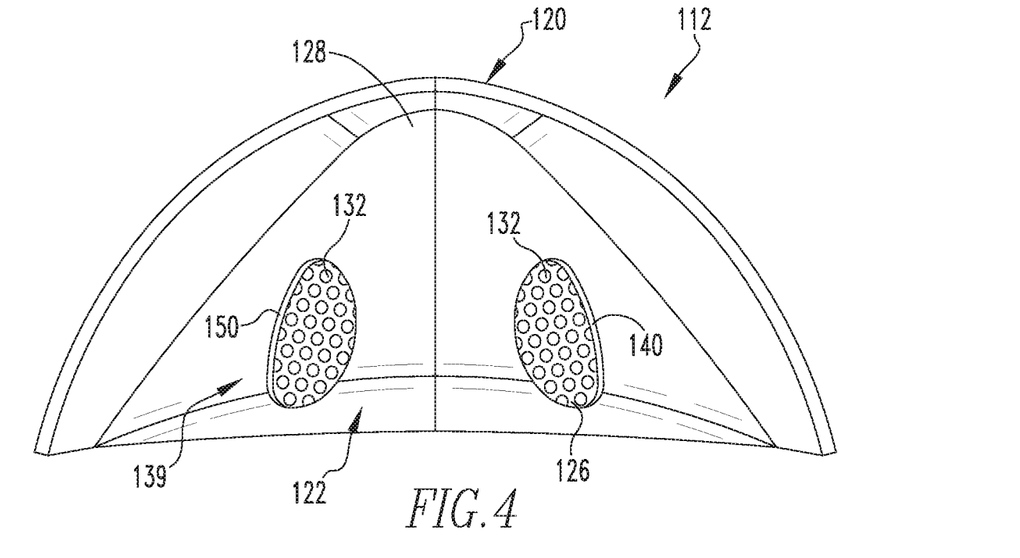
FIG. 4 is a simplified rear view of another patient interface, in accordance with another non-limiting embodiment of the disclosed concept.

FIG. 4 is a simplified rear view of another patient interface 112, in accordance with another non-limiting embodiment of the disclosed concept, that may be substituted into patient interface assembly 10 of FIG. 1 for patient interface 12. Patient interface 112 is structured similar to, and made of similar materials as, patient interface 12, discussed above, and like reference numbers represent like features. Rear portion 122 of patient interface 112 includes a support layer 126 (FIGS. 4 and 5) and a patient engaging layer 128 wherein the at least one thru hole 139 includes a first thru-hole 140 and a second thru-hole 150. Similar to first and second dense arrays 40, 50 of the arrangement of FIG. 2, each of first and second thru-holes 140, 150 are positioned to generally align with a corresponding nare of patient 8.

Figure 5:
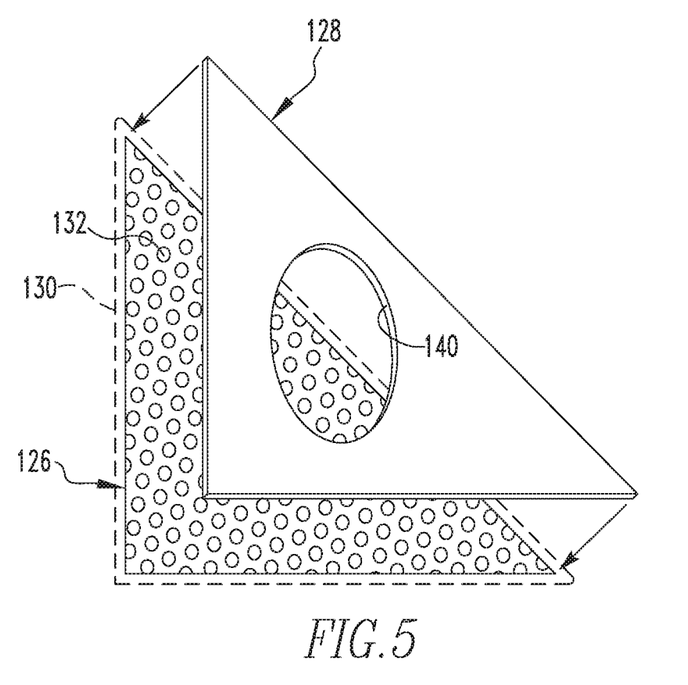
FIG. 5 is a simplified exploded view of a portion of a rear portion of the patient interface of FIG. 4 showing a patient engaging layer and support layer thereof.

Referring to FIG. 5, thru-hole 140 is defined by an edge portion surrounding an area of at least 62 mm$^2$. Similar to the embodiment of FIGS. 2 and 3 in which each of first and second dense arrays 40 and 50 overlies only a portion of region 30, first and second thru-holes 140 and 150 each overlies only a portion of region 130. Additionally, as region 130 of support layer 126 has a plurality of thru-holes 132 (only one thru-hole 132 of the plurality is numbered), patient engaging layer 128 is structured to be inflated by thru-holes 132 of support layer 126 in substantially the same manner by which thru-holes 32 of support layer 26 inflates patient engaging layer 28 as previously discussed/illustrated in regard to FIG. 1A. Accordingly, the arrangement of patient interface 112 similarly provides for an improved sealing arrangement.

In alternative example embodiments, support layer 126 and patient engaging layer 128 have been laminated together, either completely or only with selected portions thereof coupled together. In one such example, only regions of patient engaging layer 128 immediately adjacent each of first and second thru-holes 140, 150 are coupled to support layer 126. Such arrangement provides for greater stability/collapse resistance of patient engaging layer 128 about first and second thru-holes 140, 150, while still providing for improved sealing/comfort by providing for the remainder of patient engaging layer 128 to inflate toward the patient.

Figure 6:
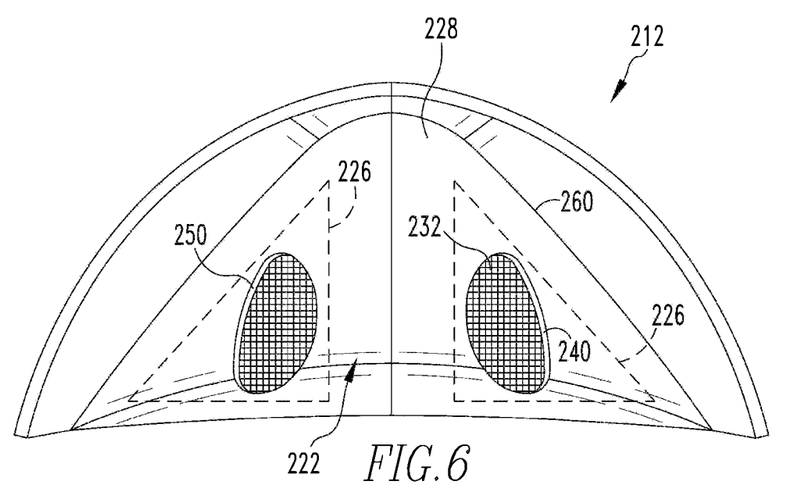
FIG. 6 is a simplified rear view of another patient interface, in accordance with another non-limiting embodiment of the disclosed concept.
Figure 7:
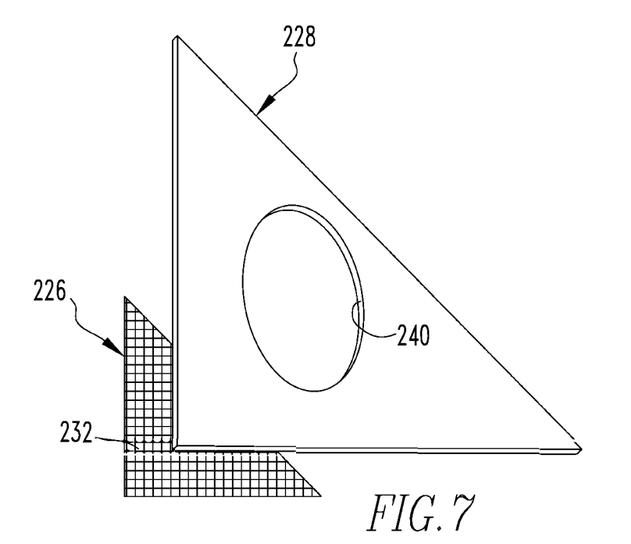
FIG. 7 is a simplified exploded view of a portion of a rear portion of the patient interface of FIG. 6 showing a patient engaging layer and a mesh member thereof.

FIG. 6 is a simplified rear view of another patient interface 212, in accordance with another non-limiting embodiment of the disclosed concept that may be substituted into patient interface assembly 10 of FIG. 1 for patient interface 12. Patient interface 212 is structured similar to patient interfaces 12 and 112, discussed above, and like reference numbers represent like features. Rear portion 222 of patient interface 212 includes a patient engaging layer 228. However, rather than including a layer sized and structured similar to support layers 26 and 126, rear portion 222 includes smaller mesh members 226 coupled to patient engaging layer 228 near first thru-hole 240 and second thru-hole 250. Mesh member 226 has a plurality of thru-holes 232 (only one thru-hole 332 of the plurality is numbered). Mesh members 226 may be coupled to the cavity facing side, the patient facing side, or generally in the same plane as patient engaging layer 228.

Continuing to refer to FIG. 6, patient engaging layer 228 has a perimeter 260, and in one example embodiment each of mesh members 226 are spaced from periphery 260. Compare, for example, FIG. 6 to FIGS. 1A and 2, in which outer perimeter 60 of patient engaging layer 28 substantially overlies the entire outer perimeter 70 of support layer 28. As such, each mesh member 226 may be a component that is relatively easily secured and/or attached to patient engaging layer 228 at a localized region, e.g., proximate thru-holes 240, 250, rather than along an entire periphery of patient engaging layer 28 and overlying the periphery.

Figure 8:
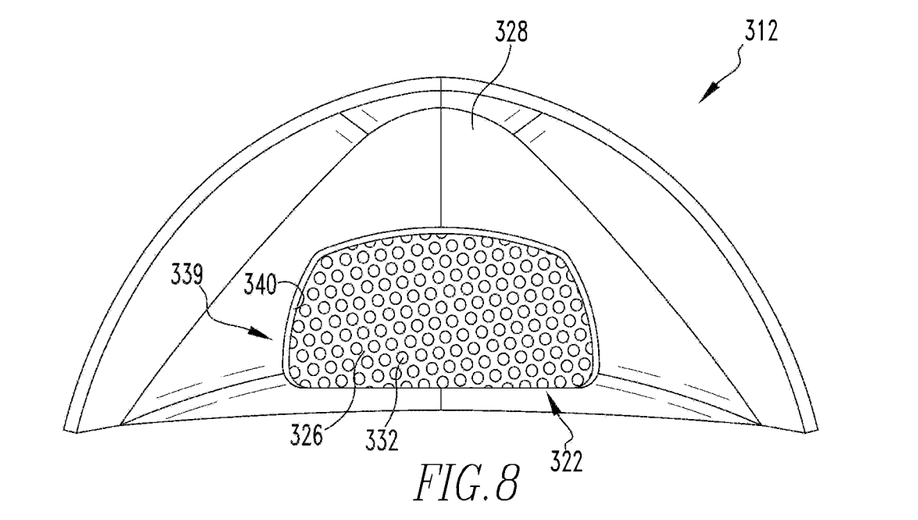
FIG. 8 is a simplified rear view of another patient interface, in accordance with yet another non-limiting embodiment of the disclosed concept.
Figure 9:
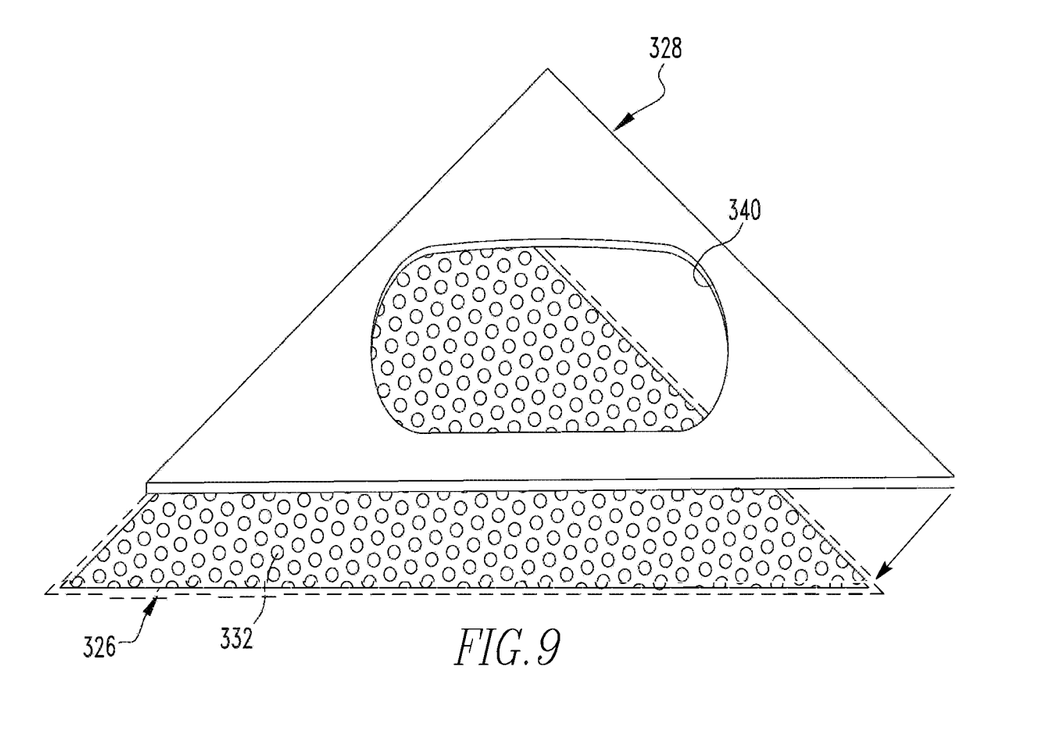
FIG. 9 is a simplified exploded view of a portion of a rear portion of the patient interface of FIG. 8 showing a patient engaging layer and a support layer thereof.

FIG. 8 is a simplified rear view of another patient interface 312, in accordance with another non-limiting embodiment of the disclosed concept, that may be substituted into patient interface assembly 10 of FIG. 1 for patient interface 12. Patient interface 312 is structured similar to, and made of similar materials as, patient interfaces 12 and 112, discussed above, and like reference numbers represent like features. Rear portion 322 of patient interface 312 includes a support layer 326 (FIGS. 4 and 5) and a patient engaging layer 328 wherein the at least one thru hole 339 is single thru-hole 340 which is positioned to generally align with both of the nares of patient 8.

Figure 10:
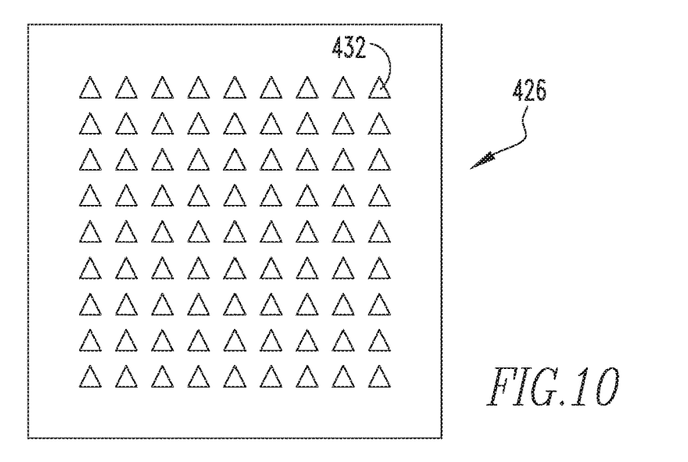
FIGS. 10-12 are simplified views of different support layers that may be used in patient interfaces in accordance with other non-limiting embodiments of the disclosed concept.
Figure 11:
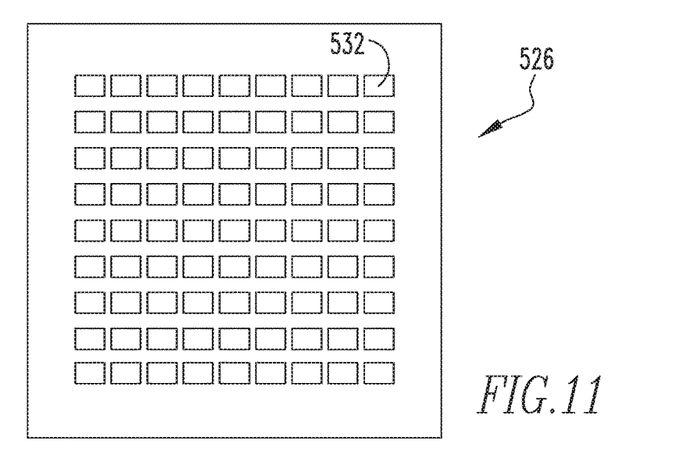
Figure 12:
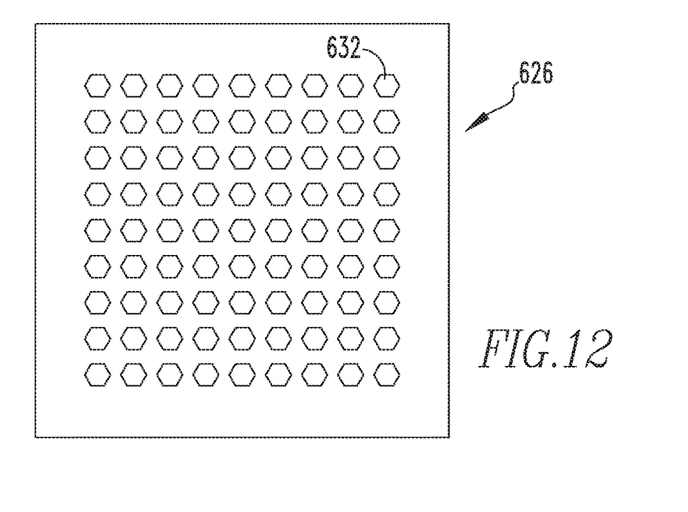

While patient interfaces 12, 112 and 312 included support layers 26, 126 and 326 having generally circular-shaped thru-holes (e.g., 32, 132, 332), it is to be appreciated that thru-holes having other geometries are also contemplated herein. For example, FIGS. 10-12, respectively, show simplified views of support layers 426, 526, 626 having triangular-shaped thru-holes 432, rectangular-shaped thru-holes 532, and hexagonal-shaped thru-holes 632 in accordance with other example embodiments of the disclosed concept.

From the foregoing examples it is thus to be appreciated that the disclosed concept provides for an improved (e.g., without limitation, more comfortable, better seal) patient interface 12, 112, 212, 312 for use in a patient interface assembly 10 in delivering a flow F of breathing gas to the airway of a patient 8.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface for use in delivering a flow of breathing gas to an airway of a patient, the patient interface comprising:
    a front portion; and
    a rear portion coupled to the front portion, the front portion and the rear portion together defining a cavity therebetween which is structured to receive the flow of breathing gas, the rear portion including:
        a support layer disposed directly adjacent the cavity, the support layer comprising a region having a plurality of first thru-holes structured to receive the flow of breathing gas from the cavity, and
        a patient engaging layer structured to engage the patient at or about the airway of the patient, the patient engaging layer comprising at least a second thru-hole structured to receive the flow of breathing gas from the plurality of first thru-holes,
    wherein the second thru-hole comprises a first thru-hole structured to generally align with a first nare of a patient and a second thru-hole structured to generally align with a second nare of the patient.

2. The patient interface of claim 1, wherein the second thru-hole overlies only a portion of the region.

3. The patient interface of claim 1, wherein the support layer has an outer perimeter; and wherein the patient engaging layer has an outer perimeter substantially overlaying the entire outer perimeter of the support layer and being coupled thereto.

4. The patient interface of claim 1, wherein the patient engaging layer is coupled to the support layer adjacent the second thru-hole.

5. The patient interface of claim 1, wherein the patient engaging layer is made of an elastic fabric material.

6. The patient interface of claim 5, wherein the support layer is made of a fabric material.

7. The patient interface of claim 1, wherein the plurality of first thru-holes comprises a dense array of thru-holes.

8. The patient interface of claim 1, wherein each of the plurality of first thru-holes has a shape selected from the group consisting of circular-shaped, triangular-shaped, honeycomb-shaped, and rectangular-shaped.

9. The patient interface of claim 1, wherein the support layer comprises a mesh member coupled to the patient engaging layer adjacent the second thru-hole.

10. The patient interface of claim 1, wherein the support layer comprises a first mesh member coupled to the patient engaging layer adjacent the first thru-hole and a second mesh member coupled to the patient engaging layer adjacent the second thru-hole.

11. A patient interface for use in delivering a flow of breathing gas to an airway of a patient, the patient interface comprising:

a front portion; and a rear portion coupled to the front portion, the front portion and the rear portion together defining a cavity therebetween which is structured to receive the flow of breathing gas, the rear portion including:

a support layer disposed directly adjacent the cavity, the support layer comprising a region having a plurality of first thru-holes structured to receive the flow of breathing gas from the cavity, and a patient engaging layer structured to engage the patient at or about the airway of the patient, the patient engaging layer comprising at least a second thru-hole structured to receive the flow of breathing gas from the plurality of first thru-holes, wherein the second thru-hole comprises a dense array of thru-holes.

12. The patient interface of claim 11, wherein the second thru-hole is structured to generally align with both of the nares of a patient.

13. A patient interface for use in delivering a flow of breathing gas to an airway of a patient, the patient interface comprising:

a front portion; and a rear portion coupled to the front portion, the front portion and the rear portion together defining a cavity therebetween which is structured to receive the flow (F) of breathing gas, the rear portion including:

a support layer disposed directly adjacent the cavity, the support layer comprising a region having a plurality of first thru-holes structured to receive the flow of breathing gas from the cavity, and a patient engaging layer structured to engage the patient at or about the airway of the patient, the patient engaging layer comprising at least a second thru-hole structured to receive the flow of breathing gas from the plurality of first thru-holes, wherein the second thru-hole comprises a first dense array of thru-holes structured to generally align with a first nare of a patient and a second dense array of thru-holes structured to generally align with a second nare of the patient.

* * * * *